US007655659B2

(12) United States Patent
Yarosh et al.

(10) Patent No.: US 7,655,659 B2
(45) Date of Patent: Feb. 2, 2010

(54) **BIOMIMETIC OF *EVODIA RUTAECARPA* FRUIT EXTRACT FOR AMELIORATION OF INFLAMMATION**

(75) Inventors: Daniel B. Yarosh, Merrick, NY (US); David A. Brown, Merrick, NY (US); Matthew T. Canning, East Meadow, NY (US)

(73) Assignee: Applied Genetics Incorporated Dermatics, Freeport, NY (US)

( * ) Notice: Subject to any disclaimer, the term of this patent is extended or adjusted under 35 U.S.C. 154(b) by 594 days.

(21) Appl. No.: 11/660,283

(22) PCT Filed: Aug. 11, 2005

(86) PCT No.: PCT/US2005/028630

§ 371 (c)(1),
(2), (4) Date: Feb. 15, 2007

(87) PCT Pub. No.: WO2006/023377

PCT Pub. Date: Mar. 2, 2006

(65) Prior Publication Data

US 2008/0096902 A1   Apr. 24, 2008

Related U.S. Application Data

(60) Provisional application No. 60/602,985, filed on Aug. 19, 2004.

(51) Int. Cl.
*A61K 31/497* (2006.01)
*A61K 31/44* (2006.01)

(52) U.S. Cl. .................. 514/252.17; 514/356

(58) Field of Classification Search ............ 514/252.17, 514/356
See application file for complete search history.

(56) References Cited

U.S. PATENT DOCUMENTS

| 5,592,956 | A | 1/1997 | Ju et al. |
| 5,998,421 | A | 12/1999 | Yokoo et al. |
| 6,214,831 | B1 | 4/2001 | Yokoo et al. |
| 6,239,114 | B1 | 5/2001 | Guthrie et al. |
| 6,323,241 | B1 | 11/2001 | Yeager et al. |
| 2007/0207195 | A1 | 9/2007 | Yarosh et al. |

FOREIGN PATENT DOCUMENTS

| CN | 1568998 | 1/2005 |
| JP | 59-122414 | 7/1984 |
| JP | 60-224622 | 11/1985 |
| JP | 4-305527 | 10/1992 |
| JP | 11-246423 | 9/1999 |
| KR | 2001-0018658 | 3/2001 |

OTHER PUBLICATIONS

Hu Chang-Ping, et al.; "Research progress in pharmacological actions of evodiamine and rutaecarpine;" Chinese Pharmacological Bulletin; 19(10): 1084-1087; 2003, (Eng. Abstract).
Bergman et al. Studies of Rutaecarpine and Related Quinazolinocarboline Alkaloids. J. Org. Chem. 50: 1246-1255, 1985.
Chavan et al. A Facile Total Synthesis of Rutaecarpine. Tetrahedron Letters. 45: 997-999, 2004.
Chiou et al. Comparative Study on the Vasodilatory Effects of Three Quinazoline Alkaloids Isolated from *Evodia rutaecarpa*. J. Nat. Prod. 59: 374-378, 1996.
Coverly et al. Susceptibility to skin stinging, non-immunologic contact uticaria and acute skin irritation; is there a relationship? Contact Dermatitis 38:90-95, 1998.
Duteil et al. Objective assessment of topical corticosteroids and non-steroidal anti-inflammatory drugs in methyl-nicotinate-induced skin inflammation. Clin. Exp. Dermatol 15:195-199, 1990.
Gupta, S. The Role of Phytopharmaceuticals in Topical Pain Relief. HAPPI Dec. 2001, p. 110.
Issachar et al. Correlation between percutaneous penetration of methyl nicotinate and sensitive skin, using laser Doppler imaging. Contact Dermatitis 39:182-186, 1998.
Kobayashi et al. Capsaicin-Like Anti-Obese Activities of Evodiamine from Fruits of *Evodia rutaecarpa*, a Vanilloid Receptor Agonist. Planta Med. 67: 628-633, 2001.
Kobayashi et al. The Positive Ionotropic and Chronotropic Effects of Evodiamine and Rutaecarpine, Indoloquinazoline Alkaloids Isolated from the Fruits of *Evodia rutaecarpa*, on the Guinea-Pig Isolated Right Atria: Possible Involvement of Vanilloid Receptors. Planta Med. 67:244-248, 2001.
Kobayashi, Y. The Nociceptive and Anti-Nociceptive Effects of Evodiamine from fruits of *Evodia rutaecarpa* in Mice. Planta Med. 69:425-428, 2003.
Mahns, et al. Contribution of UVB and UVA to UV-dependent stimulation of cyclo-oxygenase-2 expression in artificial epidermis. Photochem. Photobiol. Sci. 3:257-262, 2004.
Matsuda et al. Antinociceptive Activities of 70% Methanol Extract of Evodia Frutus (Fruit of *Evodia rutaecarpa* var. bodinieri) and Its Alkaloidal Components. Biol. Pharm. Bull. 20 (3) 243-248, 1997.
Matsuda, et al. Antinociceptive and anti-inflammatory activities of limonin isolated from the fruits of *Evodia rutaecarpa* var. bodinieri. Planta Med. May; 64(4):339-42, 1998.
Moon, et al. A new class of COX-2 inhibitor, Rutaecarpine from *Evodia rutaecarpa*. Inflamm. Res. 48: 621-625, 1999.

(Continued)

*Primary Examiner*—Raymond J Henley, III

(57) ABSTRACT

Compositions and methods are provided for reversing and/or inhibiting inflammation, e.g., by inhibiting prostaglandin and/or COX-2 production, using one or more indolequinazoline alkaloids, preferably in combination with butylated hydroxytoluene. The preferred indolequinazoline alkaloids are rutaecarpine, evodiamine, and dehydroevodiamine, which are naturally found in unpurified form in the traditional Chinese medicine Wu Chu Yu made from the fruit of the herb, *Evodia rutaecarpa*.

19 Claims, 7 Drawing Sheets

OTHER PUBLICATIONS

Figure 1:
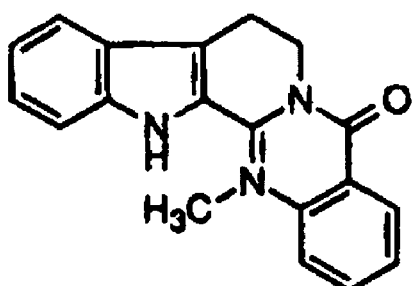
Figure 1:
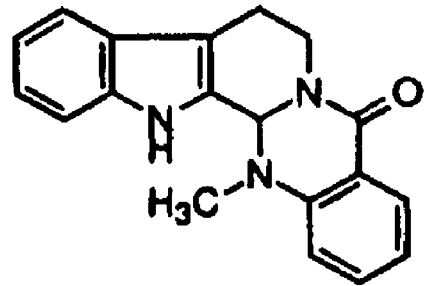
Figure 1:
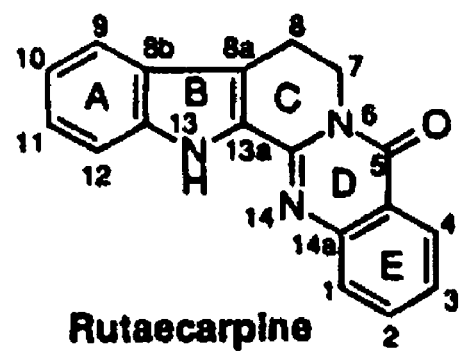

Morrow et al. Identification of skin as a major site of prostaglandin $D_2$ release following oral administration of niacin in humans. J. Invest. Dermatol. 98:812-815, 1992.

Sheu, J-R. Pharmacological Effect of Rutaecarpine, an Alkaloid Isolated from *Evodia rutaecarpa*. Cardiovascular Drug Rev. 17:237-245, 1999.

Thuille et al. Bactericidal activity of herbal extracts. Int. J. Hyg. Environ. Health. 206: 217-221, 2003.

Ward et al. Niacin skin flush in schizophrenia: a preliminary report. Schizophrenia Res. 29:269-274.

Wilkin et al. Prostaglandins and nicotinate-provoked increase in cutaneous blood flow. Clin. Pharmacol. Ther. 38:273-277, 1985.

Woo et al. Rutaecarpine, a quinazolinocarboline alkaloid, inhibits prostaglandin production in raw264.7 macrophages. Planta Med. 67(6):505-509, 2001.

Dehydroevodiamine

(1)

Evodiamine

(2)

Rutaecarpine

(3)

BIOMIMETIC OF *EVODIA RUTAECARPA* FRUIT EXTRACT FOR AMELIORATION OF INFLAMMATION

CROSS REFERENCE TO RELATED APPLICATIONS

This application is the U.S. national phase under 35 USC §371 of International Application No. PCT/US05/28630, filed Aug. 11, 2005, which was published in English under PCT Article 21(2) on Mar. 2, 2006 as International Publication No. WO 2006/023377. This application claims the benefit under 35 USC §119(e) of U.S. Provisional Application No. 60/602,985, filed Aug. 19, 2004.

I. FIELD OF THE INVENTION

This application relates to the preparation of a biomimetic mixture of compounds that ameliorates inflammatory effects caused by environmental and physiological conditions. In particular, the mixture biomimics an extract prepared from the fruit of *Evodia rutaecarpa*. The mixture can inhibit cyclo-oxygenase activity and can reduce the production of prostaglandins and the appearance of erythema after exposure to ultraviolet light or inflammatory chemicals.

II. BACKGROUND OF THE INVENTION

Overt inflammation at the site of a wound or infection has been well characterized at the level of tissue pathology, cell biology, microbiology, biochemistry and molecular biology. What we now understand is that these same processes at a lower level produce a state of microinflammation that presents very few clinical symptoms but that is a human health concern. The conditions that predispose to microinflammation are a consequence of both genetics and aging, so that microinflammation is more common among the elderly. The conditions include reduced vasoreactivity and increased response to environmental toxins. The results of a challenge to these conditions are an exaggerated vasodilation, influx of inflammatory cells and release of cytotoxins. This can be associated with erythema and pain, but often this cycle of challenge and response is chronic and presents symptoms only at later stages. Microinflammation of this type may be responsible for much of heart disease, Alzheimer's disease, arthritis, cancer and many other chronic diseases which finally manifest themselves in the elderly.

Important mediators of both acute and microinflammation are prostaglandins (PG). PG synthesis from the precursor arachidonic acid is controlled by the cyclo-oxygenases (COX) enzymes. The family of PG signals many responses, such as vasodilation, and activation of inflammatory cells. A basal level of PG is maintained by COX-1, which is necessary for normal cell metabolism. In response to noxious stimuli, COX-2 is induced and activated, producing a superabundance of PG that leads to many inflammatory responses. Unfortunately, as we age, the resting level of COX-2 increases, and therefore the production of PG in response to a stimulus also increases.

Modulators of PG are widely sought after because of the enormous market for their effects. Very successful new pharmaceutical chemical entities have been commercialized that selectively inhibit COX-2 and thereby inhibit the inflammatory responses characteristic of aging. These modulators should be well-defined, consistent and selective in their actions to avoid side-effects, especially since they may be used over long periods of time and by the elderly.

Botanical extracts prepared from plants are believed by some members of the scientific community to influence PG production and to have anti-inflammatory effects. An example is the extract produced from the *Evodia rutaecarpa* fruit, which is known in traditional Chinese medicine as Wu-Chu-Yu. The extract alone and combined with other botanical extracts has been described as an anti-inflammatory agent, an antineoplastic agent, a skin whitening treatment, an anti-hypertensive, an extract for providing skin with wetness and increase in gloss, and a treatment for pain, among many other claims. These extracts contain many organic compounds that have been studied individually, and various effects have been attributed to the individual components, the major ones being the indolequinazoline alkaloids. These are also known as quinazolindocarboline alkaloids and in *Evodia* fruit they are primarily rutaecarpine, evodiamine and dehydroevodiamine. The *Evodia* fruit is not common or easily grown, and the relative amounts of the compounds in the extract prepared from the fruit vary greatly by the time of year, geographic location, year of the harvest, as well as the extraction and preservation method, and many other variables. All these factors have contributed to the lack of commercialization of this extract.

It is also desirable to have a convenient test system to measure the inhibition of the microinflammatory response in human skin, which generates both nitric oxide (NO) and PG, has no long-lasting effects and is not harmful to the subject. Current methods for testing inhibition of inflammation involve the use of strong irritants, such as sodium lauryl sulfate, carrageenan or Balsam of Peru. These produce vigorous and sometimes painful inflammatory reactions. Methyl nicotinate (MN) has been used to generate a flushing response as a method of diagnosing schizophrenia. Susceptibility to skin stinging has been suggested to be related to over-reaction to methyl nicotinate (Issachar et al., 1998), but this has been contradicted (Coverly et al., 1998). Methyl nicotinate induced inflammation is inhibited by inhibitors of PG (Wilkin et al, 1985).

III. SUMMARY OF THE INVENTION

In accordance with a first aspect, the invention provides a composition comprising:
 a) one or more indolequinazoline alkaloids;
 b) butylated hydroxytoluene; and
 c) one or more solvents and/or one or more carriers;

wherein the combined concentrations of the one or more indolequinazoline alkaloids in the composition is at least 0.02 µg/ml and the concentration of butylated hydroxytoluene is at least 0.01 mg/ml.

In accordance with a second aspect, the invention provides a composition comprising:
 a) one or more indolequinazoline alkaloids;
 b) butylated hydroxytoluene; and
 c) one or more solvents and/or one or more carriers;

wherein the sum of the dry weights of (a) and (b) in the composition is at least 10 percent of the weight of total solids in the composition (preferably at least 50 percent, more preferably, at least 90 percent).

In connection with this aspect of the invention, the dry weight of (b) in the composition is preferably at least 50 weight percent of the total solids in the composition.

In accordance with a third aspect, the invention provides a composition comprising:

a) one or more indolequinazoline alkaloids;
b) butylated hydroxytoluene; and
c) one or more solvents and/or one or more carriers;

wherein the quotient of the light absorption of the composition at 550 nanometers divided by its absorption at 270 nanometers is less than or equal to 0.01.

In accordance with a fourth aspect, the invention provides a composition comprising:
a) one or more indolequinazoline alkaloids;
b) butylated hydroxytoluene; and
c) one or more solvents and/or one or more carriers;

wherein the quotient of the light absorption of the composition at 450 nanometers divided by its absorption at 400 nanometers is less than or equal to 0.1.

In accordance with the foregoing aspects, the composition preferably comprises butylene glycol, i.e., as a solvent and/or carrier.

In accordance with a fifth aspect, the invention provides a composition comprising:
a) one or more indolequinazoline alkaloids; and
b) butylene glycol.

In accordance with this aspect, the composition can also comprise butylated hydroxytoluene.

In accordance with a sixth aspect, the invention provides a method for at least partially reversing and/or at least partially inhibiting skin inflammation of a mammal comprising applying to the skin of a mammal in need of such a reversal and/or inhibition a composition comprising (a) one or more indolequinazoline alkaloids having a purity greater than or equal to 50% (preferably, greater than or equal to 90%) when used to formulate the composition; and (b) butylated hydroxytoluene.

In accordance with a seventh aspect, the invention provides a method for at least partially reversing and/or at least partially inhibiting skin inflammation of a mammal comprising applying to the skin of a mammal in need of such a reversal and/or inhibition a composition comprising:
a) one or more indolequinazoline alkaloids; and
b) butylated hydroxytoluene;

wherein the anti-inflammatory activity of the composition when tested using a methyl nicotinate induced erythema on human skin is substantially the same or greater than the anti-inflammatory activity of a composition which consists of butylene glycol in which is dissolved the same percentage weights by volume of the one or more indolequinazoline alkaloids and the butylated hydroxytoluene in the composition.

In accordance with the sixth and seventh aspects of the invention, the composition preferably comprises butylene glycol.

In accordance with an eight aspect, the invention provides a method for at least partially inhibiting the activity of cyclo-oxygenase-2 comprising administering to mammalian skin in need of such inhibition a composition comprising butylated hydroxytoluene, or tricyclo(3,3,1,1(3,7)-decane-1-carboxylic acid ethyl ester, or a combination of butylated hydroxytoluene and tricyclo(3,3,1,1(3,7)-decane-1-carboxylic acid ethyl ester, wherein the concentration of butylated hydroxytoluene, or tricyclo(3,3,1,1(3,7)-decane-1-carboxylic acid ethyl ester, or the combination of butylated hydroxytoluene and tricyclo(3,3,1,1(3,7)-decane-1-carboxylic acid ethyl ester in the composition is effective in at least partially inhibiting the activity of cyclo-oxygenase-2.

In accordance with this aspect, the composition preferably comprises butylene glycol.

In accordance with a ninth aspect, the invention provides a method for inducing the skin of a mammal to produce nitric oxide comprising administering a composition comprising an effective amount of methyl nicotinate to the skin of a mammal which exhibits symptoms of impaired circulation, e.g., the skin exhibits erythromelalgia or Reynaud's syndrome.

In accordance with a tenth aspect, the invention provides a method for preparing a composition which can be used in a formulation which is to be applied to mammalian skin comprising:
a) providing a first component comprising an indolequinazoline alkaloid;
b) providing a second component comprising butylated hydroxytoluene;
c) providing a carrier and/or a solvent suitable for application to mammalian skin; and
d) using the first component, the second component, and the carrier and/or solvent to prepare the composition;

wherein the purity of the indolequinazoline alkaloid in the first component is greater than or equal to 50 percent (preferably, greater than or equal to 90 percent).

In accordance with an eleventh aspect, the invention provides a method for preparing a formulation for application to mammalian skin comprising:
a) providing a first component comprising an indolequinazoline alkaloid;
b) providing a second component comprising butylated hydroxytoluene;
c) providing a carrier and/or a solvent suitable for application to mammalian skin; and
d) using the first component, the second component, and the carrier and/or solvent to prepare the formulation;

wherein the purity of the indolequinazoline alkaloid in the first component is greater than or equal to 50 percent (preferably, greater than or equal to 90 percent).

In connection with the tenth and eleventh aspects of the invention, the carrier and/or solvent preferably comprises butylene glycol.

In accordance with various of the foregoing aspects, the compositions and methods of the invention preferably have some or all of the following characteristics:

(1) the combined concentrations of the one or more indolequinazoline alkaloids in the composition is approximately 400-600 µg/ml;

(2) the one or more indolequinazoline alkaloids are individually selected from the group consisting of rutaecarpine, evodiamine, dehydroevodiamine, and their salts;

(3) the concentration of butylated hydroxytoluene is at least 0.05 mg/ml;

(4) the concentration of butylated hydroxytoluene is 4-6 mg/ml and the combined concentrations of the one or more indolequinazoline alkaloids in the composition is approximately 400-600 µg/ml;

(5) the composition further comprises evodine;

(6) the composition further comprises one or more agents which inhibit the production of prostaglandins;

(7) the composition further comprises one or more agents which have the potential to stimulate the production of prostaglandins;

(8) the combined concentrations of the one or more indolequinazoline alkaloids in the composition are effective to at least partially reverse and/or at least partially inhibit inflammation;

(9) the combined concentrations of the one or more indolequinazoline alkaloids and the butylated hydroxytoluene in the combination are effective to at least partially reverse and/or at least partially inhibit inflammation;

(10) the composition is in the form of an emulsion; and/or

(11) the composition is suitable for application to mammalian skin, e.g., human skin.

It is to be understood that both the foregoing general description and the following detailed description are merely exemplary of the invention, and are intended to provide an overview or framework for understanding the nature and character of the invention.

Additional features and advantages of the invention are set forth in the detailed description which follows, and in part will be readily apparent to those skilled in the art from that description or recognized by practicing the invention as described herein. The accompanying drawings are included to provide a further understanding of the invention, and are incorporated in and constitute a part of this specification.

IV. BRIEF DESCRIPTION OF THE DRAWINGS

FIG. 1. Chemical structures of dehydroevodiamine, evodiamine and rutaecarpine.

Figure 2:
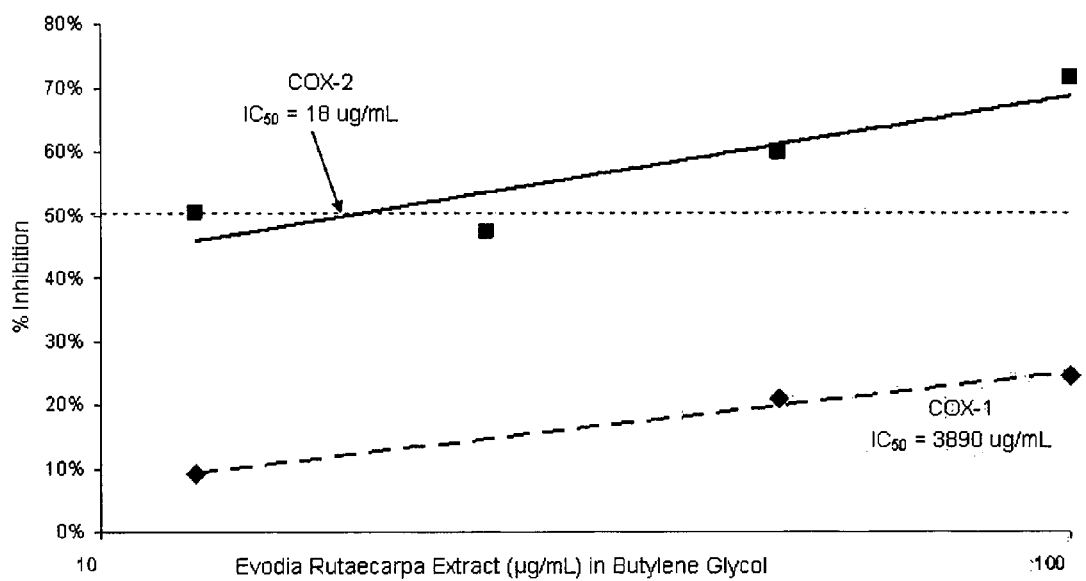

FIG. 2. Plots of the inhibitory concentration (IC) for 50% reduction of COX-1 and COX-2 in vitro by *Evodia rutaecarpa* extract using butylene glycol as a vehicle.

FIG. 3. A. Inhibition of COX-2 enzyme by individual *Evodia rutaecarpa* extract fractions excised from RP-18 F254 HPTLC plates, and complete *Evodia rutaecarpa* extract (EVE) equal to the total mass of the individually analyzed fractions. B. Inhibition of COX-2 by subfractions generated by excision of fraction 17 from a RP-18 F254 HPTLC plate followed by further fractionation on a normal phase HPTLC plate. The mass of *Evodia rutaecarpa* extract (EVE) is the same as that in A.

Figure 4:
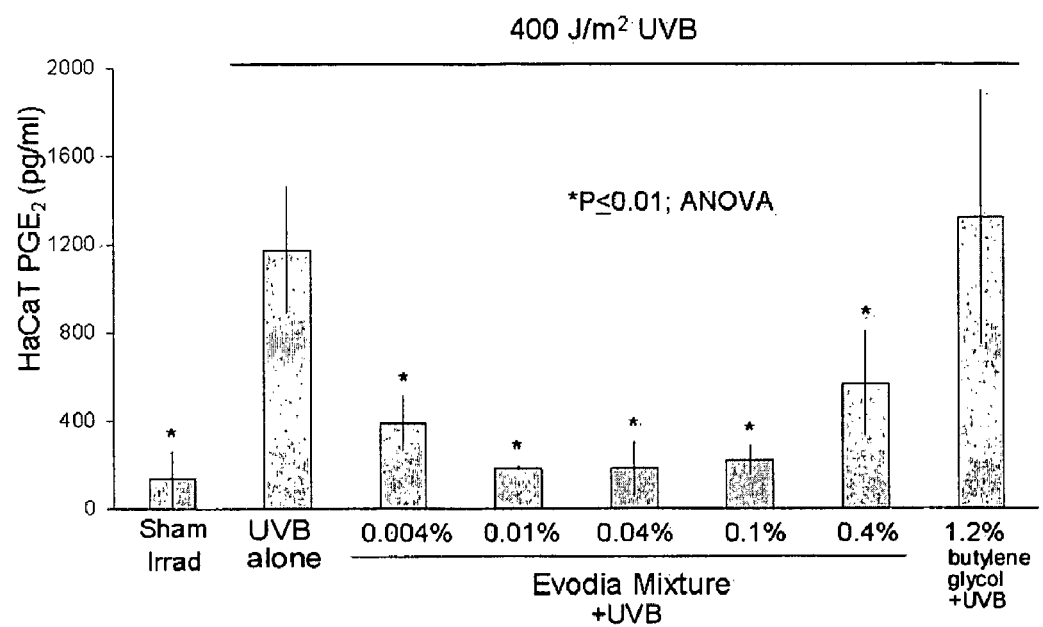

FIG. 4. Inhibition of UVB-induced $PGE_2$ secretion from HaCaT keratinocyte cells by *Evodia* mixture.

Figure 5A:
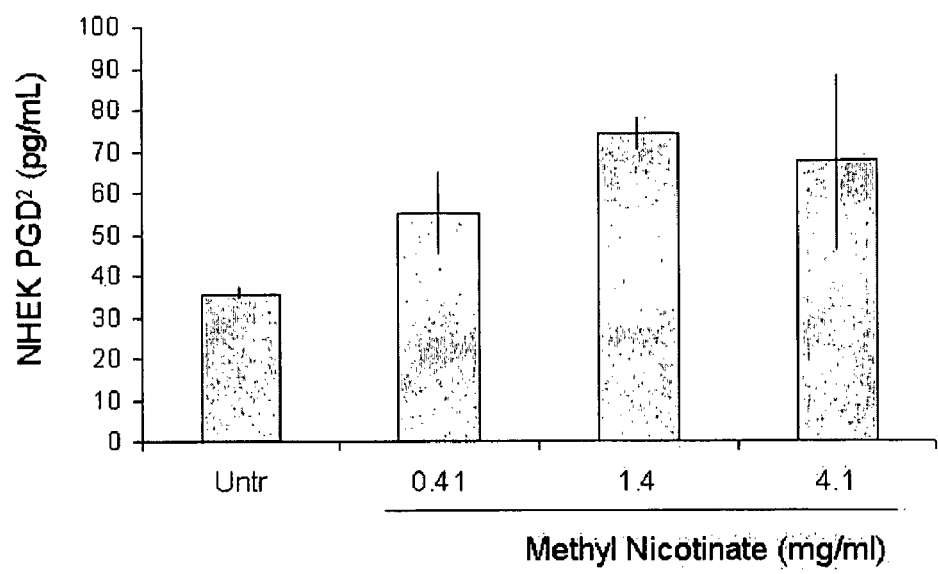
Figure 5B:
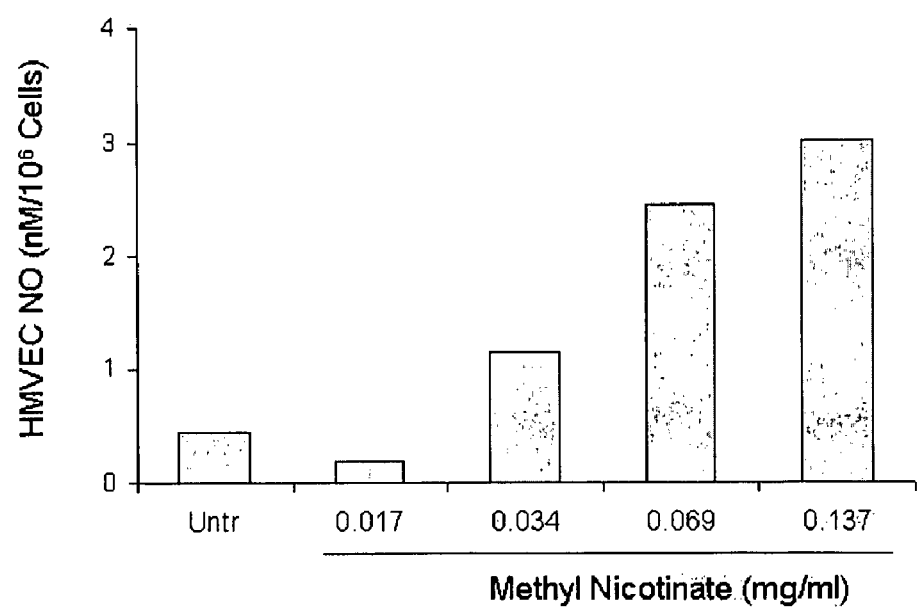

FIG. 5. A. Effect of methyl nicotinate on $PGD_2$ secretion from normal human epidermal keratinocytes (NHEK). B. Effect of methyl nicotinate on release of nitric oxide (NO) from human microvascular endothelial cells (HMVEC).

Figure 6:
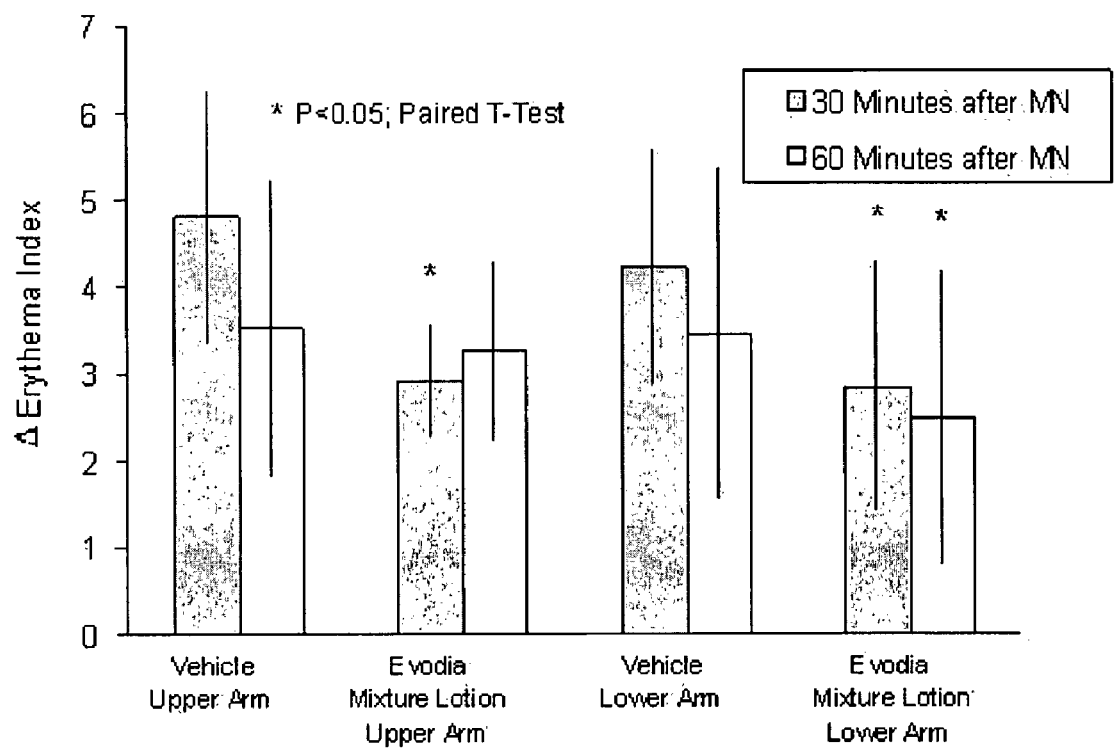

FIG. 6. Effect of a single 1% (v/v) *Evodia* mixture lotion pre-treatment on erythema induced by 0.14 mg/ml methyl nicotinate in human skin at 30 and 60 minutes after MN treatment.

Figure 7:
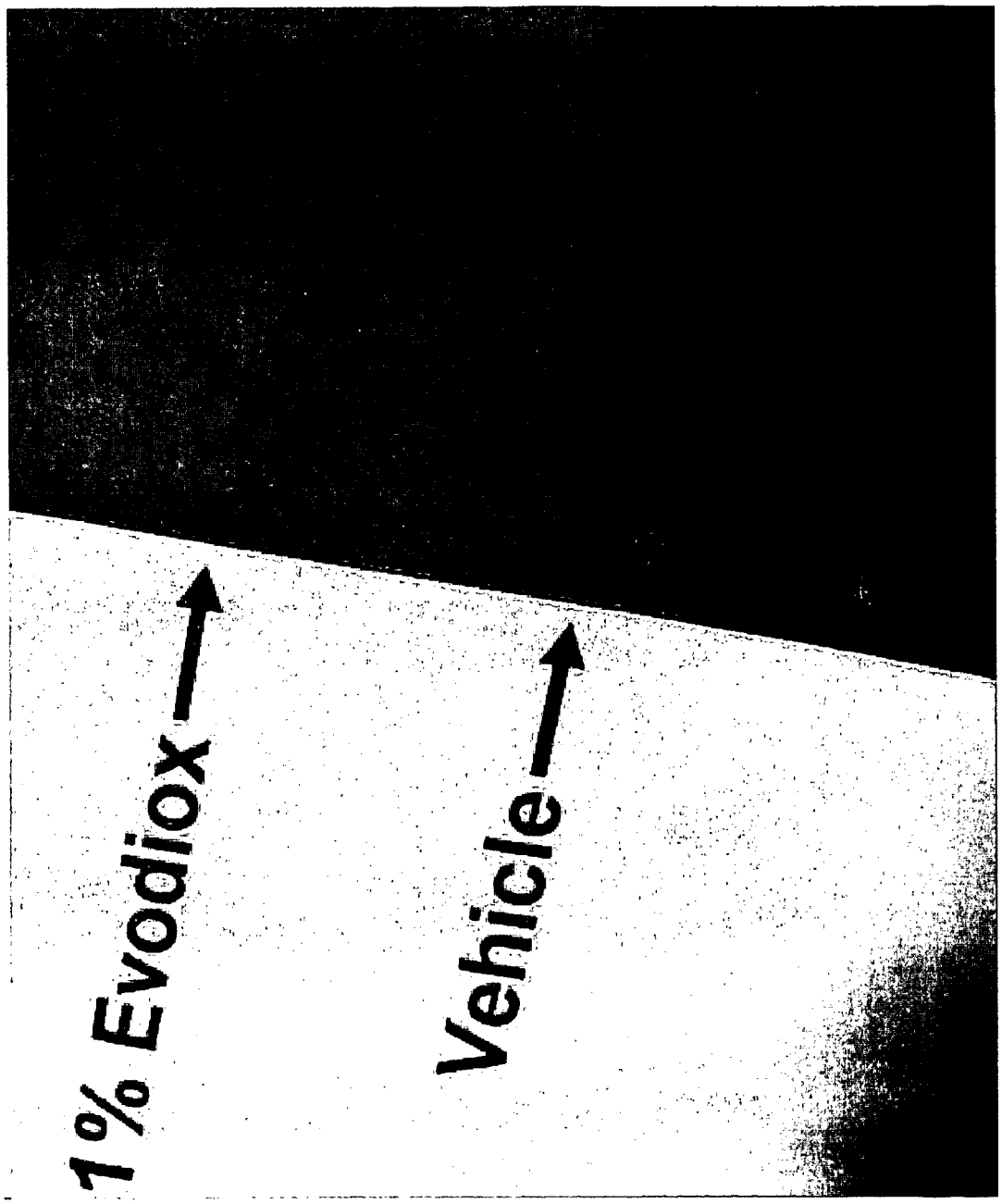

FIG. 7. Photograph of the volar forearm of a subject pretreated with either 1% (v/v) *Evodia* mixture or vehicle control and then challenged with 0.14 mg/ml methyl nicotinate. The photograph was taken 30 minutes after challenge, and the dark circle at the vehicle control site is the inducible erythema, which is virtually absent at the *Evodia* mixture treated site.

V. DETAILED DESCRIPTION OF THE INVENTION AND ITS PREFERRED EMBODIMENTS

As described in detail below, in certain of its preferred aspects, the invention provides a mixture of compounds biomimetic of *Evodia* fruit extract in a butylene glycol base that suppress the production of inflammation in a mammal, e.g., a human. The mixture can inhibit the activity of cyclo-oxygenases and can reduce the production of prostaglandins induced by exposure to ultraviolet light or chemical agents. The mixture can inhibit the appearance of an inflammatory response in, for example, the skin.

As used herein, the word "biomimetic" refers to a human-made substance or composition that in at least part of its function, imitates, at least in part, the function of a natural substance or composition. In accordance with this definition, the present invention in certain of its embodiments, relates to a biomimetic of *Evodia* fruit extract and, in particular, a biomimetic with regard to the reported anti-inflammatory properties of this extract.

As discussed below, several *Evodia* fruit extract preparations were obtained and analyzed, and found to differ greatly in composition and concentration of the indolequinazoline alkaloids. As described in Example 1, it was found that the extract with the highest concentration of these alkaloids inhibited COX-2 enzyme activity and reduced UVB-induced PG release. In the course of these experiments, it was surprisingly discovered that the solvent butylene glycol accentuated the activity of the extract (Example 1). It was also unexpectedly found that by weight rutaecarpine and evodiamine were less effective in inhibiting UVB-PG release when mixed in the extract with other components than when in the purified form (Example 2). This demonstrated to us that an inhibitor of the alkaloids was present in the extract.

Analysis of the *Evodia rutaecarpa* fruit extract by high performance thin layer chromatography (HPTLC) revealed many bands, indicating a complex mixture of compounds. The pattern of bands varied among batches of fruit and lots of extraction, and the potency of the anti-inflammatory activity also varied. After analyzing the individual fractions in various preparations, we came to the conclusion that the COX-2 inhibitory activity was not found among the indolequinazoline alkaloid fractions, but rather in two separate fractions (Example 2). This was contrary to the prior art, which taught that the inhibition of UVB-induced PG release was due to inhibition of COX-2 (Andre Mahns, Rainer Wolber, Franz Stab, Lars-Oliver Klotz and Helmut Seis. Contribution of UVB and UVA to UV-dependent stimulation of cyclo-oxygenase-2 expression in artificial epidermis. Photochem. Photobiol. Sci. 3:257-262, 2004), and that the COX-2 inhibition was due to the indolequinazoline alkaloids (Moon et al., 1999 and Gupta, 2001). We had found that the alkaloids inhibited UVB-induced PG release without effect on COX-2, but something else was inhibiting COX-2.

Analysis of the two COX-2 inhibitory fractions revealed that they were butylated hydroxytoluene, a widely used synthetic antioxidant, and tricyclo(3,3,1,1[3,7]-decane-1-carboxylic acid ethyl ester, a natural fragrance (Example 2) We replicated the COX-2 inhibitory activity using pure BHT (Example 2). Since BHT is synthetic it cannot be a natural component of the *Evodia* fruit. No mention of BHT was made in the documents from the factory that supplied the extract. We examined two separate lots of *Evodia* fruit extract from the same factory, and one lot (#030124) contained the BHT fraction and showed anti-COX-2 activity, while a second lot (#030702) did not contain the BHT fraction and did not have anti-COX-2 activity. We concluded that BHT was not intentionally included in the *Evodia* fruit extract by the factory, and that it was a contaminant from a solvent sporadically used in extraction or that it was frequently lost at a later time during processing.

From these discoveries of the true nature of the anti-inflammatory activities in the *Evodia rutaecarpa* fruit extract, we prepared a preferred biomimetic by mixing indolequinazoline alkaloids with butylated hydroxytoluene in a butylene glycol base (Example 3). Indolequinazoline alkaloids include rutaecarpine, dihydrorutaecarpine, 14-formyldihydrorutaecarpine, evodiamine, dehydroevodiamine, isoevodiamine, hydroxyevodiamine (rhesinine), evocarpine, dihydroevocarpine and wuchuyine, and methods for their synthesis have been described (Bergman and Bergman, 1985, Chavan and Sivappa, 2003). The indolequinazoline alkaloids that are currently being synthesized and thus are available in commercial quantities at greater than 90% (w/w) purity are rutaecarpine, evodiamine and dehydroevodiamine, and accordingly these indolequinazoline alkaloids are preferred. The compounds are structurally related (see FIG. 1). Dehydroevodiamine (structure 1) interchanges with evodiamine (structure 2) by protonation of N-14 in the D-ring, and they are functional homologs.

In order to produce a product that is more closely biomimetic of Evodia rutaecarpa extract, it is desirable to include one or more non-alkaloid compounds that are found in the Evodia fruit. These include rutaevin, evodine (also known as limonin), evodol, evodinone, evogin, and gushuyic. It is also desirable if the one or more non-alkaloids have some anti-inflammatory activity, such as that of evodine as described in Matsuda et al, 1998 and shown in Example 2. Further, because consumers prefer clear or white topical products, the one or more non-alkaloids should have little absorption in the visible light range. The one or more non-alkaloids should be safe and commercially available in purity greater than 90% (w/w), and evodine meets these criteria. Under some commercial marketing conditions it is preferable if at least one purified component in the biomimetic mixture is not synthetic but rather is purified from an extract of the Evodia plant, and highly purified (>90% (w/w) pure) evodine extracted from the plant fruit seeds can be obtained from China. For these reasons, a preferred non-alkaloid compound is purified natural evodine.

The preferred biomimetic of the invention is thus a mixture of indolequinazoline alkaloids, evodine and butylated hydroxytoluene (with, optionally, an antimicrobial agent, such as, phenoxyethanol). This mixture is referred to herein as the Evodia mixture (Example 3). It is a lightly colored product while Evodia extracts are typically darkly colored. We have found that the mixture of these purified components produces a synergistic effect in inhibition of UVB-induced PG release that is greater than the sum of the effects that would be expected for the individual components, as described in Example 3. Further, this Evodia mixture was able to dramatically reduce inflammation in human skin induced by methyl nicotinate, after only 60 minutes of application (Example 4). Even at a 1000-fold dilution (i.e., 0.1% (v/v)), the mixture was effective in preventing inflammation in human skin when used over two weeks (Example 4).

It should be noted that the Evodia mixture differs from natural Evodia fruit and natural Evodia fruit extract in a variety of ways. For example, it is a change in character from natural Evodia fruit extract because it lacks the natural inhibitors of anti-inflammatory activity, and always contains BHT, a compound never found in Evodia fruit, and not consistently found in extracts. Furthermore, the Evodia mixture contains some Evodia fruit extract components but not others, and together with a non-natural compound it produces a synergistic interaction. These results are not an inherent characteristic or a natural consequence of the fruit extract.

Each individual component of the Evodia mixture, as well as the entire mixture, may be dissolved in any suitable solvent, but because the compounds are lipophilic, the preferred solvent is non-polar or organic. The individual components or the Evodia mixture may also be encapsulated in a delivery vehicle, such as a liposome, niosome, ethosome, transferosome, microsponge, or other rigid or flexible encapsulation system, which is then added to the final product. It is often desirable to include an agent to prevent microbial contamination, and a favored anti-microbial is phenoxyethanol, which is recommended by its manufacturer to be used at a concentration of 1%.

Since the solvent may be applied topically, it should be safe and not irritating. Suitable solvents include alcohol, but this can be a fire hazard in storage and shipping, and propylene glycol, which can be irritating to some people. As described in Example 1, the anti-inflammatory activities are unexpectedly greater when the components are dissolved in butylene glycol than in alcohol. For these reasons the preferred solvent for topical administration is butylene glycol. The individual compounds or Evodia mixture may be added to any cosmetic or pharmaceutically acceptable base, either polar or non-polar in nature, or a base with a combination of polar and non-polar phases.

When the individual components or the Evodia mixture are added to an aqueous or polar phase, an emulsion may be formed, and it may be desirable to add the smallest amount of the non-polar individual compound or mixture relative to the polar phase to facilitate the formation of the emulsion. For this reason, it is desirable to have the individual compounds or the Evodia mixture at the highest practical concentration in the non-polar solvent, that is, near their limits of solubility. Therefore the upper limit in preparation of the mixture is their limits of solubility in the polar solvent.

The Evodia mixture is effective over a wide range of concentrations, from 0.01 µg/ml to 500 mg/ml of active components (i.e. indolequinazoline alkaloids, evodine and butylated hydroxytoluene) in the topical preparation. As described in Example 4, lower concentrations are effective when used over a longer period of time. Higher concentrations are effective in a shorter period of time. For example, 0.1% (v/v) of the Evodia mixture (containing a total of 6.08 µg/ml of the active components) is effective when used on the skin twice daily for seven days. On the other hand, 1% (v/v) of the Evodia mixture (containing a total of 60.8 Hg/ml of the active components) is effective on the skin within 60 minutes after application. The selection of the appropriate concentration will take into account the expense of the product, the frequency and length of time that it will be used, and the potential for unexpected reactions. Low cost, frequent and long usage and concern for adverse events, e.g., allergic reactions, will favor lower concentrations. An especially preferred use level for the preparation applied to the skin is 4-7 µg/ml indolequinazoline alkaloid(s), 0.2-0.4 µg/ml evodine and 40-60 µg/ml butylated hydroxytoluene.

The anti-inflammatory effects may be achieved by using the Evodia mixture itself, or by adding additional components not derived from Evodia fruit, or other chemicals or extracts. These additional components may be additional COX-2 inhibitors, or inhibitors of COX-1 or phospholipase A2. They may be additional preventive agents such as sunscreens or sun blocks, or antioxidants. They may be nutrients such as vitamins or minerals, or particular metabolic modifiers such as retinoic acid or hormones. There may also be agents which have the potential to stimulate the production of prostaglandins, e.g., coloring agents, fragrances, and antiperspirants In such cases, the Evodia mixture can serve to mask the inflammatory side effects of these potentially PG-stimulating agents.

The Evodia mixture may be used before, during, or after any insult that induces an inflammatory response either directly or indirectly. However, the mixture requires about 45 minutes after application to the target tissue before its anti-inflammatory effects are observed. Therefore, the preferred time of use is at least 45 minutes, and preferable 60 minutes, before the irritant. For example, the Evodia mixture can be applied 60 minutes prior to sun exposure. For practical purposes, because some types of inflammatory insult are not anticipated, the *Evodia* mixture is preferably used once in the morning or, more preferably, twice daily in the morning and evening.

The range of initiators of inflammation which the *Evodia* mixture can ameliorate is quite extensive. It includes any inducer of the conversion of arachidonic acid into prostaglandins. The source may be external environmental stimuli or internal stimuli resulting from normal metabolic processes or disease. Examples of external stimuli are ionizing or non-ionizing radiation, heat, oxidation, abrasion, wounding, noxious agents, food, allergens or infectious agents. Examples of internal stimuli include changes in metabolism, hormone, paracrine or autocrine imbalance, nervous or neurological stimuli, cancer or autoimmune response.

The *Evodia* mixture may be formulated in any suitable cosmetic or pharmaceutical carrier. For topical application, this can include topical creams, lotions, serums, milks, emulsions, gels, shampoos, hair rinses, solid forms, powders, waxes and two- or multiple component mixing systems for application to the face, neck, arms or hands, legs or feet, trunk, abdomen, hair, scalp or mucus membranes.

The *Evodia* mixture may be used to treat healthy people who experience inflammation, or people suffering from disease with an inflammatory component. It may be used to treat infants, children, adults or the aged. The *Evodia* mixture may also be used to treat people who do not have any symptoms of inflammatory disease, including those with a predisposition due to the presence of genes, mutant genes or special forms of genes that make the individual more likely to suffer from inflammation (see U.S. Provisional Applications Nos. 60/577,822 and 60/578,530, filed Jun. 8, 2004 and Jun. 10, 2004, respectively, by inventors Daniel B. Yarosh and David A. Brown and entitled "Genetic Screening for Polymorphisms in Human Genes That Increase or Decrease Sensitivity to Toxic Agents," the entire contents of both of which are incorporated herein by reference). In one preferred embodiment, a topical lotion is used to treat people over forty years of age who present with complaints about skin sensitivity to environmental insults.

The anti-inflammatory activity of the *Evodia* mixture can be demonstrated in many models using irritants and allergens such as sodium lauryl sulfate, carrageenan or balsam of Peru (Myroxylon pereirae resin). These inflammatory inducers cause a sometimes painful reaction that is expressed over 24 hours and whose effects last for days. A preferred method for demonstration is in inhibition of the methyl nicotinate response. A solution of methyl nicotinate applied to the skin rapidly induces a flushing reaction that peaks in 15 to 60 minutes and resolves in about 3 hours. The amount of methyl nicotinate required for the optimal response varies from individual to individual, in a range of 0.1 mM to 30 mM, while in a large majority of cases an adequate response is achieved with 1 mM. The response contains the essential elements of induction of PG and NO. Pre-treatment of skin with a formulation containing a relatively high concentration of the *Evodia* mixture for 60 minutes, and even a relatively low concentration for 2 weeks, reduces the initial peak of erythema and shortens the time until the reaction subsides.

Without intending to restrict in any way the scope of the invention, the following examples are presented to illustrate various of the invention's aspects and its use.

EXAMPLE 1

Inhibition of COX-2 and UV-induced PGE2 Release from Skin Cells by *Evodia rutaecarpa* Extract Four lots of *Evodia rutaecarpa* extract were obtained from a Chinese supplier. The extracts were prepared by extraction with 50% grain alcohol, and ranged in form from a brown, sticky paste to a green slime. The four lots had rutaecarpine content of 2.2% (w/w) (lot 020420), 0.5% (w/w) (lot 20929), 0.3% (w/w), (lot 020621) and 4% (w/w) (lot 030124), as determined by HPTLC using purified rutaecarpine (Sigma-Aldrich, St. Louis, Mo., USA) as a standard. The extract supplier explained this disparity by noting that the herbal source was different for each lot and the content of rutaecarpine therefore varies among the lots. Seeds from the fruit are usually harvested in the summer season, so in winter it is difficult to obtain high quality raw herbs.

The HaCaT keratinocyte cell line was cultured in Gibco-BRL (Grand Island, N.Y.) D-MEM low glucose medium containing 10% heat inactivated fetal bovine serum, 1% penicillin/streptomycin, 1% L-glutamine, and 1% nonessential amino acids. Immediately after irradiation with UVB (400 $J/m^2$), HaCaT cells were treated with 12.5 µg/ml to 100 µg/ml *Evodia rutaecarpine* extract (lot 030124) in ethanol. The media was harvested 24 hours after UVB irradiation and analyzed for prostaglandin E2 ($PGE_2$) content using a $PGE_2$ ELISA kit (R & D Systems Catalogue Number DE0100). Results showed inhibition of UVB-induced $PGE_2$ secretion from HaCaT cells ranging from 29% at 12.5 µg/ml *Evodia rutaecarpa* extract to 78% at 100 µg/ml.

It is well known that the major source of inducible prostaglandin release from cells is related to induction of cyclo-oxygenase 2 (COX-2). Therefore, an in vitro assay was performed using purified COX-2 to determine if *Evodia rutaecarpa* extract could directly inhibit the COX-2 enzyme. The assay was a commercially available COX Inhibitor Screening Assay (Cayman, Ann Arbor, Mich.) run according to the manufacturer's instructions. Results showed inhibition of in vitro purified COX-2 enzyme activity ranging from 25% at 12.5 µg/ml to 61% at 100 µg/ml *Evodia rutaecarpa* extract dissolved in ethanol, and 50% at 12.5 µg/ml to 71% *Evodia rutaecarpa* extract dissolved in 1,3-butylene glycol (as used in the specification and claims, 1,3-butylene glycol or 1,3-butanediol is referred to as "butylene glycol"). The inhibitory concentration for 50% reduction (IC50) of COX-2 in vitro by *Evodia rutaecarpa* extract dissolved in ethanol was 57 µg/ml while the IC50 for *Evodia rutaecarpa* extract dissolved in butylene glycol was 18 µg/ml. These results show that *Evodia rutaecarpa* extract is a COX-2 inhibitor, and that effectiveness as a COX-2 inhibitor is increased by dissolution of the extract in butylene glycol relative to dissolution in ethanol. Therefore, butylene glycol is a preferred vehicle.

It is well known that constitutively expressed COX-1 is a source of essential structural and regulatory PG. In contrast, COX-2 is inducible by a variety of proinflammatory stimuli, and resultant PGs can be either beneficial or harmful depending upon the level and duration of their production. It is well recognized that repression of COX-2 activity may be both preventative and curative for the adverse effects of sustained inflammation. However, repression of constitutive COX-1 activity may be detrimental since the products of COX-1 are essential. Therefore, it is common practice to express the efficacy of anti-inflammatory cyclo-oxygenase inhibitors as a function of their ability to selectively repress COX-2 relative to COX-1. Measurement of IC50s for COX-1 and COX-2 showed that *Evodia rutaecarpa* extract is 216-fold more inhibitory for COX-2 than COX-1 (FIG. 2). These results show that *Evodia rutaecarpa* extract is a selective COX-2 inhibitor, and they indicate that *Evodia rutaecarpa* extract may inhibit UVB-induced $PGE_2$ secretion from cells by repressing COX-2 activity.

EXAMPLE 2

Inhibition of COX-2 and UV-induced PGE2 Release from Skin Cells by Purified Components of *Evodia rutaecarpa* Extract Since one of the *Evodia rutaecarpa* extracts that was effective contained 3% (w/w) evodiamine and 4% (w/w) rutaecarpine dissolved in ethanol (lot 030124, as determined by HPTLC), it was suspected that either or both of these agents might be responsible for inhibiting UVB-induced $PGE_2$ secretion from cells, and COX-2 activity in vitro. Furthermore, there is a suggestion from the literature that rutaecarpine is a COX-2 inhibitor (Moon et al., 1999, Gupta, 2001).

We were surprised to find that both purified rutaecarpine (Sigma-Aldrich, St. Louis, Mo., USA) and evodiamine (EnviroTest Laboratories, Edmonton, Alberta, Canada) inhibited $PGE_2$ secretion from UVB-irradiated HaCaT cells at lower concentrations than when in the *Evodia rutaecarpa* extract (Table 1). 100 µg/ml of *Evodia* extract (Lot 030124), containing 4 µg/ml of rutaecarpine and 3 µg/ml of evodiamine, was required to inhibit $PGE_2$ secretion by 80%, while either purified rutaecarpine or evodiamine was equally as effective at 0.3 µg/ml. This data demonstrates that an inhibitor is present in the *Evodia* extract that prevents the indolequinazoline alkaloids from expressing their full activity.

We would expect that if the *Evodia rutaecarpa* extract inhibited UVB-induced $PGE_2$ by inhibiting COX-2, then the purified indolequinazoline alkaloids would also be COX-2 inhibitors at similar concentrations. We were surprised to find that, while the indolequinazoline alkaloids in the extract were effective COX-2 inhibitors at less than 1 µg/ml, it required substantially more of the pure rutaecarpine or pure dehydroevodiamine (a functional homolog of evodiamine) to inhibit COX-2 in vitro, i.e., >7.5 µg/ml for dehydroevodiamine and 14.4 µg/ml for rutaecarpine. (Table 2). These results suggested that another component of the extract was responsible for the COX-2 inhibitory activity.

Therefore, *Evodia rutaecarpa* extract was fractionated using HPTLC, and the individual fractions were analyzed for COX-2 inhibitory activity.

HPTLC was done using 20×20 cm RP-18 F254 plates with hexane:acetone (3:1) as the mobile phase. A total of 10 mg of *Evodia rutaecarpa* extract was loaded along the origin, adjacent to rutaecarpine and evodiamine standards. The HPTLC was run until the solvent front reached the top of the plate. When dry, the plate was visualized under a UVA lamp and the edges of all visible bands were marked. Twenty equal sized bands were marked on the area of the plate containing visible bands, and then each band was scraped from the plate. Evodiamine and rutaecarpine were removed as distinct single bands in fractions 9 and 10, respectively. Fractions were recovered from the HPTLC matrix by solubilization in ethanol followed by centrifugation at 600×g to remove residual matrix.

Figure 3A:
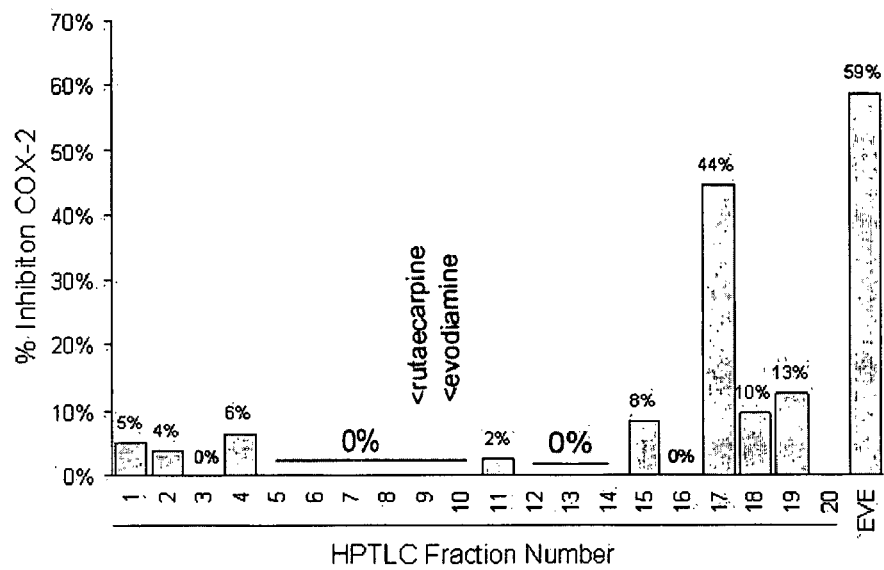

Fractions were analyzed for COX-2 inhibitory activity using the in vitro assay employed in the previous example. Results showed COX-2 inhibitory activity in Fraction 17 that was substantially equivalent to unfractionated *Evodia rutaecarpa* extract run at mass equal to the combined 20 fractions (FIG. 3A). Of particular interest was that the bands corresponding to rutaecarpine (fraction 9) and evodiamine (fraction 10) did not show COX-2 inhibitory activity in this assay, likely because any inhibitory activity required higher concentration of the indolequinazoline alkaloids. The presence of the COX-2 inhibitory activity in fraction 17 and the absence of COX-2 inhibitory activity in the fractions corresponding to the indolequinazoline alkaloids led us to believe that the COX-2 inhibitory activity of *Evodia rutaecarpa* extract lay in a new and as yet unrecognized component.

Figure 3B:
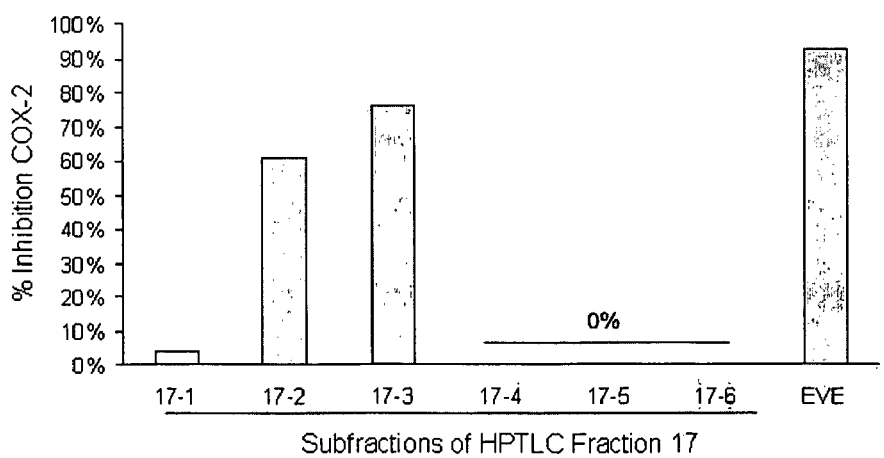

When fraction 17 was further subfractionated using normal phase HPTLC, COX-2 inhibitory activity was found in 2 of 6 bands (subfractions 17-2 and 17-3 in FIG. 3B). This activity accounted for substantially all of the COX-2 inhibitory activity in *Evodia rutaecarpa* extract (FIG. 3B).

Subfractions 17-2 and 17-3 were analyzed by gas chromatography and mass spectrometry (GCMS) by two different analyses. The first GCMS employed a 30 meter methyl silicone (ZB-1) column run at 50° C. to 300° C. at 15° C./minute in a JEOL GCmate using electron ionization mode. The compounds were identified by searching a Wiley mass spectral library. The second GCMS employed a 30 meter methyl silicone (ZB-1) column run at 50° C. to 300° C. at 15° C./minute in a Finnigan MAT GCQ using both electron and chemical ionization modes. This instrument employed a NIST mass spectral library to identify compounds. Fraction 17-2 was found to contain butylated hydroxytoluene (BHT), which is a synthetic compound used as an antioxidant and not naturally found in botanicals. Subfraction 17-3 contained tricyclo(3,3,1,1 [3,7]-decane-1-caroxylic acid, ethyl ester, also known as ethyladamantane-1-carboxylate, which is a natural fragrance with a complex structure that is not now commercially available. From the GCMS data, the concentration of BHT in the *Evodia* extract lot #030124 in terms of mg of BHT per ml of the extract was at most 0.006 mg/ml. This extract had the highest level of BHT of any of the extracts obtained, and thus in all cases the BHT concentration in the extract was substantially less than 0.01 mg/ml.

Following identification of BHT as the active component in subfraction 17-2 of *Evodia rutaecarpa*, in vitro COX-1 and COX-2 assays were done using purified BHT. Results showed that BHT was active against both COX-1 and COX-2, and showed selectivity for COX-2 (Table 3). It was more selective for COX-2 than the known botanical COX-2 inhibitor ursolic acid, but less selective than the known COX-2 inhibitor CELEBREX (Table 3).

The observation that the selectivity of the *Evodia rutaecarpa* extract (216, see Example 1) was greater than the selectivity of purified BHT (87, Table 3) led us to conclude that there is synergy among the components in inhibiting COX-2. Initial data is consistent with this synergy existing also in the biomimetic of the present invention. The ability of BHT to inhibit PG secretion from UVB-irradiated HaCaT cells was examined by treating cells with BHT immediately after UVB irradiation. The media was harvested 24 hours later and analyzed for $PGE_2$ content using a $PGE_2$ ELISA kit (R & D Systems, Minneapolis, Minn., USA). BHT inhibited UVB-induced PG secretion at 2-20 µg/ml, which is in the range of the IC50 for inhibition of COX-2 in vitro.

EXAMPLE 3

Inhibition of COX-2 and UV-induced Prostaglandins in Skin Cells by a Mixture of Purified Rutaecarpine, Evodine, Dehydroevodiamine and Butylated Hydroxytoluene The above examples show three unexpected results. First, the ability of indolequinazoline alkaloids to inhibit UVB-induced $PGE_2$ is reduced when mixed in the *Evodia rutaecarpa* extract, because the extract also contains an inhibitor of the activity. Second, the ability of the *Evodia rutaecarpa* extract to inhibit COX-2 lies not in the indolequinazoline alkaloids, but in other components, one of which is BHT. This leads to a third surprising conclusion that is contradictory to the prior art, and that is that the indolequinazoline alkaloids inhibit UVB-induced $PGE_2$ at concentrations at which they are not effective COX-2 inhibitors. We further discovered that the anti-inflammatory activity was greater when the components were in butylene glycol.

In order to take advantage of this new understanding of the activity of *Evodia rutaecarpa* extract, a biomimetic mixture of purified components found in *Evodia rutaecarpa* fruit was prepared. This *Evodia* mixture contained synthetic rutaecarpine (99.9% (w/w) pure), synthetic dehydroevodiamine (>96% (w/w) pure), natural evodine (>98% (w/w) pure), and synthetic butylated hydroxytoluene (>99% (w/w) pure) dissolved in butylene glycol (99.8% (w/w) pure) (Table 4). The mixture was prepared using the following preferred procedure: The butylene glycol was heated to 40 C and the rutaecarpine was dissolved by stirring for 10 minutes. The temperature was raised to 65 C and the BHT was dissolved by stirring for 30 minutes. The temperature was then raised to 80 C and the evodine and dehydroevodiamine were dissolved by stirring for 90 minutes. The solution was then cooled to 25 C and phenoxyethanol (a preservative) was added. Preferably, the concentration of each of the indolequinazoline alkaloids rutaecarpine and dehydroevodiamine in the *Evodia* mixture is such that it is effective at inhibiting UVB-induced $PGE_2$ secretion from cells when the *Evodia* mixture is used at 0.1% (v/v). Dehydroevodiamine is a functional homolog of evodiamine, and both in our hands and in the literature it has the same activities as evodiamine. Its advantage is that it is more readily available commercially. Preferably, the concentration of BHT is effective at inhibiting UVB-induced $PGE_2$ secretion from cells when the *Evodia* mixture is used at 0.04% (v/v) and effective at inhibiting COX-2 when the *Evodia* mixture is used at 1% (v/v). Preferably, evodine is added for commercial purposes because it is directly extracted from *Evodia* fruit and is reported to have some anti-inflammatory activity. Preferably, phenoxyethanol is added as an anti-microbial agent. Based on the foregoing, the preferred components of the *Evodia* mixture are as shown in Table 4.

The preferred *Evodia* mixture of Table 4 has a slight yellow tinge while *Evodia* extract appears darkly colored, sometimes a black or dark brown muddy color and sometimes a dark green color. The *Evodia* mixture can be distinguished from the extract by the substantial reduction in light absorption as the incident wavelengths increase from the yellow region (around 400 nanometers) to longer wavelengths. Absorbance is measured by a spectrophotometer using a standard 1-cm light path cuvette, and the value is corrected for background absorbance of the particular solvent used with the sample. Absorption is equal to the $\log_{10}$ of the reciprocal of transmittance, where transmittance is the fraction of incident light transmitted by the solution, i.e., transmittance equals transmitted intensity divided by incident intensity. It is important that the sample be properly diluted so that the absorbance measurement is within the linear range of the spectrophotometer measurement, and especially that it is not equal to or lower than the limit of detection of the machine. The absorbance value is the reading from the spectrophotometer multiplied by the dilution factor.

Both the *Evodia* mixture and the *Evodia* extract absorb in the yellow region, but the *Evodia* mixture absorbs much less than the *Evodia* extract beginning at slightly longer wavelengths and extending out into the visible region to at least 700 nanometers. In fact, the 100% (v/v) *Evodia* mixture described in Table 4 has virtually no absorption above background between 475 and 700 nm, while the extracts retain significant levels. As shown in Table 5, the ratio of absorbance at 550 nm to 270 nm in the preferred *Evodia* mixture is essentially 0 (i.e., the 550 nanometer measurement is below the detection limit of the spectrophotometer) while the *Evodia* extracts have ratios of $10 \times 10^{-3}$ or greater. Similarly, the ratio of absorbance at 450 nm to 400 nm is nearly 0 ($3 \times 10^{-3}$) for the *Evodia* mixture, but greater than $100 \times 10^{-3}$ for the *Evodia* extracts.

The preferred *Evodia* mixture of Table 4 was examined for its ability to inhibit UVB-induced $PGE_2$ secretion from HaCaT cells. The most effective concentration in inhibiting $PGE_2$ secretion was 0.01% (v/v), with an effective range for greater than 50% inhibition of UVB-induced $PGE_2$ from 0.004% (v/v) to 0.4% (v/v) (FIG. 4). Since the *Evodia* mixture is effective at 0.004% (v/v) in this assay, it is approximately 10-fold more potent than its most potent component in inhibiting UVB-induced $PGE_2$ when administered to cultured cells. This illustrates the discovery that the *Evodia rutaecarpa* extract contains a compound which blocks this activity and that when the inhibitor is removed the components act synergistically to inhibit UVB-induced $PGE_2$. The preferred *Evodia* mixture was also effective at inhibiting the COX-2 enzyme in vitro. A 1% (v/v) solution of the preferred *Evodia* mixture of Table 4 resulted in a 54% reduction of COX-2 activity, while a 2% (v/v) solution resulted in an 84% reduction of COX-2. The concentration of BHT in a 1% (v/v) *Evodia* mixture is 55 µg/ml (Table 4), indicating that the IC50 for COX-2 is similar to that of BHT when used alone in the COX-2 assay (Table 3). These results indicate that the *Evodia* mixture will have the greatest impact on COX-2 when used at 1% to 2% (v/v). Thus, while the *Evodia* mixture is useful for inhibiting UVB-induced $PGE_2$ secretion from skin cells when used at 0.01% (v/v) (FIG. 4), for inflammatory conditions mediated exclusively by COX-2, the preferred formulation would contain at least 1% (v/v) *Evodia* mixture.

EXAMPLE 4

Inhibition of Methyl Nicotinate-induced Erythema in Skin by a Mixture of Purified Rutaecarpine, Evodine, Dehydroevodiamine and Butylated Hydroxytoluene in Butylene Glycol It is thought that the application of methyl nicotinate to skin induces a transitory erythema that is mediated by PG. Both PG and NO are known to induce erythema in human skin, and PG is known to induce NO. Application of methyl nicotinate to skin has been used both as a diagnostic procedure for schizophrenia (Ward et al., 1998), and for evaluating topically applied anti-inflammatory drugs (Duteil et al., 1990). We found that methyl nicotinate is useful for inducing PG secretion from cultured skin cells, and as a means of examining the efficacy of topically applied *Evodia* mixture. Furthermore, whereas previous studies have indicated that the effects of methyl nicotinate are mediated by induction of PG secretion, we found that methyl nicotinate also induces NO, and at much lower concentrations than are needed for induction of PG. Therefore, application of methyl nicotinate to the skin to induce erythema is useful for testing agents that inhibit both prostaglandin and nitric oxide production.

Normal human epidermal keratinocytes (NHEK) and human microvascular endothelial cells (HMVEC) were obtained from a commercial supplier (Cascade Biologics, Portland, Oreg., USA) and cultured according to the manufacturer's recommendations. Methyl nicotinate was made up as a 1M stock solution in $H_2O$. The stock solution was diluted to 100 mM in $H_2O$. The 100 mM methyl nicotinate was further diluted to 125 to 1000 μM methyl nicotinate in the cell culture media and the NHEK and HMVEC cells were treated when they had grown to approximately 70% confluency with fresh media containing the methyl nicotinate. After 24 hours of incubation in the methyl nicotinate media, the cultured media was collected. Nitric oxide was measured using the Greiss reagents as described in the Calbiochem colorimetric nitric oxide assay kit (Calbiochem, San Diego, Calif.). PGs in the cell culture media were analyzed using commercially available $PGD_2$ and $PGE_2$ ELISA kits (R & D Systems, Minneapolis, Minn., USA). Results from cultured NHEK and also HMVEC show that methyl nicotinate induced both $PGD_2$ (FIG. 5A) and $PGE_2$ secretion (data not shown). This is in accordance with studies on human skin showing that erythema induced by topical application of methyl nicotinate is mediated by $PGD_2$ (Morrow et al., 1992). The tests for NO in the culture media showed that in addition to stimulating PG secretion, methyl nicotinate also induced NO secretion from HMVEC (FIG. 5B), but at much lower concentrations of methyl nicotinate than required for induction of $PGD_2$ and $PGE_2$. Since NO is a vasodilatory agent that induces skin erythema, methyl nicotinate can thus induce skin erythema by induction of NO as well as via induction of $PGD_2$ and $PGE_2$. Thus, methyl nicotinate may be useful in treatment of disease with dysfunctional microcirculation, such as erythromelalgia and Reynaud's disease A study was performed to examine the ability of a single treatment with 1% (v/v) of the preferred *Evodia* mixture (Table 4) in a 0.54% (w/v) Carbopol® hydrogel lotion to reduce erythema induced by a challenge dose of methyl nicotinate in the skin of seven human subjects. Each application area was demarked by an adjacent label made with a permanent black ink marker. One hour prior to the methyl nicotinate challenge dose, the *Evodia* mixture lotion was applied liberally to treatment spots. A Carbopol® hydrogel lotion containing no *Evodia* mixture was used as a vehicle control. Treatments were replicated on the upper and lower volar forearm of all subjects. One hour later, lotion was washed from the arm, and erythema was read in triplicate at each treatment spot using a Dermaspectrometer (Cortex Technology, Smedevaenget 10, 9560 Hadsund, Denmark). Immediately thereafter, 10 μL of a 0.14 mg/ml methyl nicotinate solution in water was applied to each treatment spot. Erythema was read 15, 30, 60 and 90 minutes later. Results showed the peak response and inhibitory effect of 1% (v/v) *Evodia* mixture lotion occurred 30 minutes after methyl nicotinate challenge (FIG. 6). An example of the difference in the erythema at the methyl nicotinate treated sites between those pretreated with the vehicle and those pretreated with the *Evodia* mixture is shown in FIG. 7. Thirty minutes after application of the methyl nicotinate, the site pre-treated with the vehicle displays a vigorous erythemic reaction, while the site pre-treated with the *Evodia* mixture has a barely perceptible reaction. Results for all the subjects were calculated as change of erythema readings from time zero. At 15 minutes after application of methyl nicotinate, not all subjects showed induction of erythema (data not shown). Thirty minutes after methyl nicotinate challenge, results were statistically significant ($P<0.05$; paired T-test) for both the upper and lower arm (FIG. 6). The average reduction of methyl nicotinate-induced erythema by 1% (v/v) *Evodia* mixture lotion was about 35% for both the upper and lower arm. By 60 minutes after methyl nicotinate application, the erythemic response had begun to fade, and consequently the effects of *Evodia* lotion on the erythemic response were less discernible. By 90 minutes, erythema readings returned to baseline.

Lower doses of the *Evodia* mixture are also effective when used over longer periods of time. The same protocol as described above was followed with five sites treated twice daily for two weeks. Three sites were treated with test articles of 0.1%, 0.3% and 1.0% (v/v) *Evodia* mixture in hydrogel lotion, one site was treated with a vehicle control lotion and one site was not treated with either lotion or methyl nicotinate. After the first week, the sites were challenged with methyl nicotinate, and the vehicle treated site showed the characteristic erythemic response compared to the untreated site. The lotions containing 0.3% and 1.0% (v/v) *Evodia* mixture inhibited methyl nicotinate induced erythema, while the 0.1% (v/v) had no measurable effect. After two weeks of twice daily treatment, the 0.1% (v/v) *Evodia* mixture, as well as the 0.3% and 1.0% (v/v) lotions, was effective in suppressing the inflammatory response.

These results show that the *Evodia* mixture reduces methyl nicotinate induced erythema in human skin. Since methyl nicotinate is known to induce NO and PG secretion in human skin, these results indicate that the *Evodia* mixture should be useful for ameliorating a number of NO and PG mediated conditions in skin including those induced by ultraviolet radiation, environmental irritants, and endogenous inflammatory agents and conditions.

Bisabolol is the active ingredient in the anti-inflammatory herb chamomile and is widely used as a topical agent and in tea for reducing inflammatory responses. A side by side comparison was made between the *Evodia* mixture and bisabolol, each formulated in a hydrogel lotion, with bisabolol equal to the total amount of actives in the *Evodia* mixture. Results showed that 1% (v/v) *Evodia* mixture lotion (Table 4, 60.8 μg/ml) was effective in reducing methyl nicotinate mediated erythema, while the bisabolol lotion (61 μg/ml) was ineffective.

Although specific embodiments of the invention have been described and illustrated, it is to be understood that a variety of modifications which do not depart from the scope and spirit of the invention will be evident to persons of ordinary skill in the art from the foregoing disclosure. As just one example, although the following claims recite various features of the invention, it is to be understood that the invention encompasses any and all combinations of those features, irrespective of whether such combination is currently set forth in the appended set of claims.

LITERATURE REFERENCES

Studies of *Evodia* Fruit Extracts and its Components:
1. Jan Bergman and Solveig Bergman. Studies of Rutaecarpine and Related Quinazolinocarboline Alkaloids. J. Org. Chem. 50: 1246-1255, 1985.

2. Subhash Chavan and R. Sivappa. A Facile Total Synthesis of Rutaecarpine. Tetrahedron Letters. 45: 997-999, 2004.
3. Wen-Fei Chou, Jyh-Fei Liao, and Chieh-Fu Chen. Comparative Study on the Vasodilatory Effects of Three Quinazoline Alkaloids Isolated from *Evodia rutaecarpa*. J. Nat. Prod. 59: 374-378, 1996.
4. Shyam Gupta. The Role of Phytopharmaceuticals in Topical Pain Relief. HAPPI December 2001, p110.
5. Yoshinori Kobayashi. The Nociceptive and Anti-Nociceptive Effects of Evodiamine from Fruits of *Evodia rutaecarpa* in Mice. Planta Med. 69:425-428, 2003.
6. Yoshinori Kobayashi, Yumiko Nakano, Miho Kizaki, Kiyoko Hoshikuma, Yoshiharu Yokoo, and Toshikazu Kamiya. Capsaicin-Like Anti-Obese Activities of Evodiamine from Fruits of *Evodia rutaecarpa*, a Vanilloid Receptor Agonist. Planta Med. 67:628-633, 2001.
7. Yoshinori Kobayashi, Kiyoko Hoshikuma, Yumiko Nakano, Yoshiharu Yokoo, and Toshikazu Kamiya. The Positive Ionotropic and Chronotropic Effects of Evodiamine and Rutaecarpine, Indoloquinazoline Alkaloids Isolated from the Fruits of *Evodia rutaecarpa*, on the Guinea-Pig Isolated Right Atria: Possible Involvement of Vanilloid Receptors. Planta Med. 67:244-248, 2001.
8. Hideaki Matsuda, Jian-xin Wu, Toshiyuki Tanaka, Munekazu Iinuma, and Michinori Kubo. Antinociceptive Activities of 70% Methanol Extract of *Evodia* Fructus (Fruit of *Evodia rutaecarpa* var. bodinieri) and Its Alkaloidal Components Biol. Pharm. Bull. 20 (3) 243-248, 1997.
9. H. Matsuda, M. Yoshikawa, M. Linuma, M. Kubo. Antinociceptive and anti-inflammatory activities of limonin isolated from the fruits of *Evodia rutaecarpa* var. bodinieri. Planta Med. May; 64(4):339-42, 1998.
10. T. C. Moon, M. Murakami, I. Kudo, K. H. Son, H. P. Kim, S. S. Kang, and H. W. Chang. A new class of COX-2 inhibitor, Rutaecarpine from *Evodia rutaecarpa*. Inflamm. Res. 48: 621-625, 1999.
11. Joen-Rong Sheu. Pharmacological Effect of Rutaecarpine, an Alkaloid Isolated from *Evodia rutaecarpa*. Cardiovascular Drug Rev. 17:237-245, 1999.
12. Nikolaus Thuille, Manfred Fille, Markus Nagl. Bactericidal activity of herbal extracts. Int. J. Hyg. Environ. Health. 206: 217-221, 2003.
13. H. G. Woo. C. H. Lee, M. S. Noh, J. J. Lee, Y. S. Jung, E. J. Baik, C. H. Moon, S. H. Lee. Rutaecarpine, a quinazolinocarboline alkaloid, inhibits prostaglandin production in raw264.7 macrophages. Planta Med. 67(6):505-9, 2001.

Studies on the Mechanism of Action of Methyl Nicotinate:
14. J. Coverly, L. Peters, E. Whittle and D. Basketter. Susceptibility to skin stinging, non-immunologic contact uticaria and acute skin irritation; is there a relationship? Contact Dermatitis 38:90-95, 1998.
15. I. Dutel, C. Queille, M. Poncet, J. P. Ortonne, and J. Czemielewski. Objective assessment of topical corticosteroids and non-steroidal anti-inflammatory drugs in methyl-nicotinate-induced skin inflammation. Clin. Exp. Dermatol 15:195-9, 1990.
16. N. Issachar, Y. Gall, M. Borrel and M-C. Poelman. Correlation between percutaneous penetration of methyl nicotinate and sensitive skin, using laser Doppler imaging. Contact Dermatitis 39:182-186, 1998.
17. J. D. Morrow, J. A. Awad, J. A. Oates, and L. J. Roberts, 1992, Identification of skin as a major site of prostaglandin $D_2$ release following oral administration of niacin in humans. J. Invest. Dermatol. 98:812-5.
18. P. E. Ward, J. Sutherland, E. M. T. Glen, and A. I. M. Glen. 1998. Niacin skin flush in schizophrenia: a preliminary report. Schizophrenia Res. 29:269-74.
19. Jonathan Wilkin, Glenn Fortner, Linda Reinhardt, Otero Flowers, S. James Kilpatrick and W. Carson Streeter. Prostaglandins and nicotinate-provoked increase in cutaneous blood flow. Clin. Pharmacol. Ther. 38:273-277, 1985.

PATENT REFERENCES

1. U.S. Pat. No. 5,998,421 and U.S. Pat. No. 6,214,831 are related to food or other compositions containing evodiamine, rutaecarpine or extracts from *Evodia* that have anti-obesity activity.
2. U.S. Pat. No. 6,323,241 discloses the use of *Evodia rutaecarpa* extract and its components as vasoactive agents for the purpose of treating erectile dysfunction.
3. U.S. Pat. No. 6,239,114 discloses the use of evodin, here referred to as limonin, as an anti-cancer agent in combination with other compounds.

The contents of the documents cited above under the headings "Studies of *Evodia* fruit extracts and its components," "Studies on the mechanism of action of methyl nicotinate" and "Patents" are incorporated herein by reference.

TABLE 1

Inhibition of UVB-Induced $PGE_2$ secretion in HaCaT cells by *Evodia rutaecarpa* extract and purified components

| Test article | μg/ml to inhibit 80% of $PGE_2$ secretion |
|---|---|
| *Evodia rutaecarpa* extract | 100 |
| Indolequinazoline alkaloids contained in *Evodia rutaecarpa* extract -- 7% (w/w) comprising 4% (w/w) rutaecarpine and 3% (w/w) evodiamine | 7 |
| 99+% (w/w) rutaecarpine | 0.3 |
| 98+% (w/w) evodiamine | 0.3 |

TABLE 2

Inhibition of in vitro COX-2 activity by *Evodia rutaecarpa* extract and purified components

| Test article | μg/ml to inhibit 50% of COX-2 activity |
|---|---|
| *Evodia rutaecarpa* extract | 12.5 |
| Indolequinazoline alkaloids contained in *Evodia rutaecarpa* extract -- 7% (w/w) comprising 4% (w/w) rutaecarpine and 3% (w/w) evodiamine | 0.9 |
| 99+% (w/w) rutaecarpine | 14.4 |
| 96% (w/w) dehydroevodiamine | >7.5 |

TABLE 3

The relative COX-1 and COX-2 inhibitory activity of ursolic acid, butylated hydroxytoluene, and Celebrex.

| Compound | IC50 (μg/ml) | | Selectivity |
| | COX-1 | COX-2 | COX-1/COX-2 |
|---|---|---|---|
| Ursolic Acid (URA) | 132 | 27 | 4.9 |
| Butylated Hydroxytoluene (BHT) | 1300 | 15 | 87 |
| CELEBREX | 5.7 | 0.015 | 380 |

TABLE 4

Preferred Components of *Evodia* mixture.

| Compound | µg/ml (100% (v/v)) | µg/ml when used at 1% (v/v) | µg/ml when used at 0.4% (v/v) | µg/ml when used at 0.1% (v/v) | µg/ml when used at 0.004% (v/v) |
|---|---|---|---|---|---|
| Rutaecarpine | 360 | 3.6 | 1.44 | 0.36 | 0.0144 |
| Dehydroevodiamine | 188 | 1.9 | 0.75 | 0.19 | 0.0075 |
| Evodine | 30 | 0.3 | 0.12 | 0.03 | 0.0012 |
| BHT | 5500 | 55 | 22 | 5.5 | 0.22 |
| TOTAL ACTIVES | 6,078 | 60.8 | 24.31 | 6.08 | 0.243 |
| Phenoxyethanol | 10,000 | 100 | 400 | 10 | 4 |

TABLE 5

Ratio of Absorption Values for *Evodia* extract and *Evodia* mixture for a 1 centimeter cuvette.

| | Solvent | Absorbance ratio (×10³) 550 nm/270 nm | Absorbance ratio (×10³) 450 nm/400 nm |
|---|---|---|---|
| *Evodia* extract lot 20929 | Methanol | 23 | 258 |
| *Evodia* extract lot 020621 | Methanol | 14 | 138 |
| *Evodia* extract lot 0030702 | Methanol | 22 | 331 |
| *Evodia* mixture | Butylene glycol | 0 | 3 |

What is claimed is:

1. A composition comprising:
   a. one or more indolequinazoline alkaloids;
   b. butylated hydroxytoluene; and
   c. one or more solvents and/or one or more carriers;
   wherein:
   (i) the combined concentrations of the one or more indolequinazoline alkaloids in the composition is at least 0.02 µg/ml and the concentration of butylated hydroxytoluene is at least 0.01 mg/ml; and/or
   (ii) the sum of the dry weights of (a) and (b) in the composition is at least 10 percent of the weight of total solids in the composition; and/or
   (iii) the quotient of the light absorption of the composition at 550 nanometers divided by its absorption at 270 nanometers is less than or equal to 0.01; and/or
   (iv) the quotient of the light absorption of the composition at 450 nanometers divided by its absorption at 400 nanometers is less than or equal to 0.1.

2. The composition of claim 1 wherein the sum of the dry weights of (a) and (b) in the composition is at least 90 weight percent of the total solids in the composition.

3. The composition of claim 1 wherein the dry weight of (b) in the composition is at least 50 weight percent of the total solids in the composition.

4. The composition of claim 1 wherein the one or more solvents and/or one or more carriers comprises butylene glycol.

5. A composition comprising:
   a. one or more indolequinazoline alkaloids; and
   b. butylene glycol.

6. The composition of claim 5 further comprising butylated hydroxytoluene.

7. The composition of claim 1, 5, or 6 wherein:
   (i) the combined concentrations of the one or more indolequinazoline alkaloids in the composition is approximately 400-600 µg/ml; and/or
   (ii) the one or more indolequinazoline alkaloids are individually selected from the group consisting of rutaecarpine, evodiamine, dehydroevodiamine, and their salts; and/or
   (iii) the composition further comprises evodine; and/or
   (iv) the composition further comprises one or more agents which inhibit the production of prostaglandins; and/or
   (v) the composition further comprises one or more agents which have the potential to stimulate the production of prostaglandins; and/or
   (vi) the combined concentrations of the one or more indolequinazoline alkaloids in the composition are effective to at least partially reverse and/or at least partially inhibit inflammation; and/or
   (vii) the composition is in the form of an emulsion; and/or
   (viii) the composition is suitable for application to mammalian skin; and/or
   (ix) the composition is suitable for application to human skin.

8. The composition of claim 1 or 5 wherein:
   (i) the concentration of butylated hydroxytoluene is at least 0.05 mg/ml; and/or
   (ii) the concentration of butylated hydroxytoluene is 4-6 mg/ml and the combined concentrations of the one or more indolequinazoline alkaloids in the composition is approximately 400-600 µg/ml; and/or
   (iii) the combined concentrations of the one or more indolequinazoline alkaloids and the butylated hydroxytoluene in the combination are effective to at least partially reverse and/or at least partially inhibit inflammation.

9. A method for at least partially reversing and/or at least partially inhibiting skin inflammation of a mammal comprising applying to the skin of a mammal in need of such a reversal and/or inhibition a composition comprising (a) one or more indolequinazoline alkaloids having a purity greater than or equal to 50% when used to formulate the composition; and (b) butylated hydroxytoluene.

10. The method of claim 9 wherein the one or more indolequinazoline alkaloids has a purity greater than or equal to 90% when used to formulate the composition.

11. A method for at least partially reversing and/or at least partially inhibiting skin inflammation of a mammal comprising applying to the skin of a mammal in need of such a reversal and/or inhibition a composition comprising:

a. one or more indolequinazoline alkaloids; and
b. butylated hydroxytoluene;

wherein the anti-inflammatory activity of the composition when tested using a methyl nicotinate induced erythema on human skin is substantially the same or greater than the anti-inflammatory activity of a composition which consists of butylene glycol in which is dissolved the same percentage weights by volume of the one or more indolequinazoline alkaloids and the butylated hydroxytoluene in the composition.

12. The method of claim 9 or 10 wherein:
(i) the composition comprises butylene glycol; and/or
(ii) the combined concentrations of the one or more indolequinazoline alkaloids in the composition is approximately 400-600 µg/ml; and/or
(iii) the one or more indolequinazoline alkaloids are individually selected from the group consisting of rutaecarpine, evodiamine, dehydroevodiamine, and their salts; and/or
(iv) the concentration of butylated hydroxytoluene in the composition is at least 0.05 mg/ml; and/or
(v) the concentration of butylated hydroxytoluene in the composition is 4-6 mg/ml and the combined concentrations of the one or more indolequinazoline alkaloids in the composition is approximately 400-600 µg/ml; and/or
(vi) the composition further comprises evodine; and/or
(vii) the composition further comprises one or more agents which inhibit the production of prostaglandins; and/or
(viii) the composition further comprises one or more agents which have the potential to stimulate the production of prostaglandins; and/or
(ix) the composition is in the form of an emulsion; and/or
(x) the skin is human skin.

13. A method for at least partially inhibiting the activity of cyclo-oxygenase-2 comprising administering to mammalian skin in need of such inhibition a composition comprising butylated hydroxytoluene, or tricyclo(3,3,1,1(3,7)-decane-1-carboxylic acid ethyl ester, or a combination of butylated hydroxytoluene and tricyclo(3,3,1,1(3,7)-decane-1-carboxylic acid ethyl ester, wherein the concentration of butylated hydroxytoluene, or tricyclo(3,3,1,1(3,7)-decane-1-carboxylic acid ethyl ester, or the combination of butylated hydroxytoluene and tricyclo(3,3,1,1(3,7)-decane-1-carboxylic acid ethyl ester in the composition is effective in at least partially inhibiting the activity of cyclo-oxygenase-2.

14. The method of claim 13 wherein:
(i) the composition comprises butylene glycol; and/or
(ii) the composition is in the form of an emulsion.

15. A method for inducing the skin of a mammal to produce nitric oxide comprising administering a composition comprising an effective amount of methyl nicotinate to the skin of a mammal which exhibits symptoms of impaired circulation.

16. The method of claim 15 wherein:
(i) the skin exhibits erythromelalgia; or
(ii) the skin exhibits Reynaud's syndrome.

17. A method for preparing a composition which can be used in a formulation which is to be applied to mammalian skin comprising:
a. providing a first component comprising an indolequinazoline alkaloid;
b. providing a second component comprising butylated hydroxytoluene;
c. providing a carrier and/or a solvent suitable for application to mammalian skin; and
d. using the first component, the second component, and the carrier and/or solvent to prepare the composition;

wherein the purity of the indolequinazoline alkaloid in the first component is greater than or equal to 50 percent.

18. A method for preparing a formulation for application to mammalian skin comprising:
a. providing a first component comprising an indolequinazoline alkaloid;
b. providing a second component comprising butylated hydroxytoluene;
c. providing a carrier and/or a solvent suitable for application to mammalian skin; and
d. using the first component, the second component, and the carrier and/or solvent to prepare the formulation;

wherein the purity of the indolequinazoline alkaloid in the first component is greater than or equal to 50 percent.

19. The method of claim 17 or 18 wherein:
(i) the purity of the indolequinazoline alkaloid in the first component is greater than or equal to 90 percent; and/or
(ii) the indolequinazoline alkaloid is selected from the group consisting of rutaecarpine, evodiamine, dehydroevodiamine, and their salts; and/or
(iii) the carrier and/or solvent comprises butylene glycol.

* * * * *